US008060177B2

(12) United States Patent  (10) Patent No.: US 8,060,177 B2
Hamill  (45) Date of Patent: Nov. 15, 2011

(54) REGISTRATION OF COMPUTED TOMOGRAPHY (CT) AND POSITRON EMISSION TOMOGRAPHY (PET) IMAGE SCANS WITH AUTOMATIC PATIENT MOTION CORRECTION

(75) Inventor: James J. Hamill, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1288 days.

(21) Appl. No.: 11/714,405

(22) Filed: Mar. 6, 2007

(65) Prior Publication Data

US 2007/0232903 A1  Oct. 4, 2007

Related U.S. Application Data

(60) Provisional application No. 60/779,628, filed on Mar. 6, 2006.

(51) Int. Cl.
*A61B 5/05* (2006.01)

(52) U.S. Cl. ........................................ 600/407

(58) Field of Classification Search ........................ None
See application file for complete search history.

(56) References Cited

U.S. PATENT DOCUMENTS

| | | | |
|---|---|---|---|
| 6,307,910 B1 * | 10/2001 | Acharya et al. | 378/4 |
| 6,937,696 B1 * | 8/2005 | Mostafavi | 378/95 |
| 6,959,266 B1 * | 10/2005 | Mostafavi | 702/189 |
| 7,620,444 B2 * | 11/2009 | Le et al. | 600/428 |
| 2004/0030246 A1 * | 2/2004 | Townsend et al. | 600/427 |
| 2006/0074300 A1 * | 4/2006 | Green | 600/427 |

* cited by examiner

*Primary Examiner* — Brian Casler
*Assistant Examiner* — Saurel J Selkin
(74) *Attorney, Agent, or Firm* — Peter L. Kendall

(57) ABSTRACT

A method for combined computed tomography (CT) imaging and positron emission tomography (PET) imaging uses respiration-gated CT imaging in which the optimal criteria for CT scan gating are determined after the PET scan has been performed. After acquisition of first CT scan image data and PET scan image data with strain gauge levels being recorded, optimal gating criteria are calculated based on the strain gauge levels, and a second CT scan is then performed with triggering in accordance with the optimal gating criteria.

13 Claims, 3 Drawing Sheets

REGISTRATION OF COMPUTED TOMOGRAPHY (CT) AND POSITRON EMISSION TOMOGRAPHY (PET) IMAGE SCANS WITH AUTOMATIC PATIENT MOTION CORRECTION

CROSS-REFERENCE TO RELATED APPLICATION AND CLAIM FOR PRIORITY

This application claims priority under 35 U.S.C. §119(e) from U.S. Provisional Patent Application Ser. No. 60/779,628 filed on Mar. 6, 2006.

FIELD OF THE INVENTION

The present invention relates generally to diagnostic imaging systems. More particularly, the present invention relates to a method for simultaneously performing computed tomography (CT) scanning and positron emission tomography (PET) scanning. The present method provides improved registration between CT and PET images, and allows for improved correction of image registration for errors caused by patient movement.

BACKGROUND OF THE INVENTION

Computed tomography (CT) scanning (i.e., using an external X-ray source) and positron emission tomography (PET) scanning (i.e., using an infused radiopharmaceutical as a source of gamma ray emissions) are well known methods for diagnostic medical imaging. CT scanning employs multiple X-ray images taken in multiple directions to generate a 3-dimensional image or multiple tomographic image "slices." PET scanning employs a gamma-emitting radiopharmaceutical ingested by a patient or injected into a patient. Multiple gamma ray images are taken in multiple directions to generate a 3-dimensional PET image or multiple slices. CT and PET scanning provide different information. For example, CT scanning generally has higher resolution and is superior for providing structural data such as the structure of bones, organs, etc. PET scanning generally has lower resolution but provides more useful information regarding the functional condition of body tissues and systems such as the cardiovascular system. PET is superior for indicating the presence of soft tissue tumors or decreased blood flow to certain organs or areas of the body, for example. The complementary strengths of CT and PET scanning can be provided simultaneously by performing both methods in a single apparatus and imaging session. However, combining CT and PET scanning presents technical challenges because CT and PET require different scan times and have different sensitivities to patient motion.

PET scanning requires a relatively long duration data acquisition period on the order of about 30 minutes for a typical clinically sufficient image. Typically, a large number of PET data acquisitions are acquired at many different angles during this period. Consequently, patient movement is a problem in PET scanning. Excessive motion of a patient can result in scan failure. Thoracic cage movement caused by breathing is a significant problem in PET scanning.

By comparison, CT scanning is relatively fast and can typically be performed during one breath-hold by a patient.

Fusion of CT and PET images often is inaccurate because of inevitable patient movement and breathing. Associated problems include several types of CT artifacts, errors in the association between anatomy and PET uptake, motion blur in PET, and quantitative errors PET errors such as miscalculation of the standard uptake value due to underestimation or overestimation of attenuation.

Part of the solution to these problems is to provide gating of PET and CT scanning based on measurement of certain triggering parameters associated with respiratory motion. In particular, it is known in the art to use a strain gauge to measure the tension in a strap placed around the abdomen or chest of a patient. Signals from the strain gauge are used to develop information that can be used to gate or trigger the operation of imaging apparatus.

The accuracy of such approaches is limited by the fact that patient breathing patterns change over the time period involved in performing the diagnostic scan. This problem is illustrated in the strain gauge traces of FIG. 1. The traces show that deep, irregular breathing at one point in time can be followed by a more regular, shallower breathing pattern ten minutes later. In FIG. 1, the horizontal axis represents time, with a one minute interval between the left and right sides of each plot. The vertical axis represents the signal from the strain gauge, with smaller values corresponding to a more relaxed chest and larger values corresponding to a more expanded chest. Thus, trigger signals based on respiratory cycle alone do not solve the misregistration problem.

Accordingly, there is a need in the art for improved methods for combined CT and PET scanning. It would be particularly beneficial to provide a method for combined CT and PET scanning that can correct for inaccuracies caused by patient motion such as motion caused by respiration.

SUMMARY OF THE INVENTION

The present invention includes a method for combined computed tomography (CT) imaging and positron emission tomography (PET) imaging that overcomes the problems in the prior art. In accordance with the invention, the optimal criteria for CT scan gating are determined after the PET scan has been performed. Consequently, in accordance with the invention, after acquisition of first CT scan image data and PET scan image data with strain gauge levels being recorded, optimal gating criteria are calculated based on the strain gauge levels, and a second CT scan is then performed with triggering in accordance with the optimal gating criteria. The present invention is also applicable to other combinations of different imaging modalities, such as single photon emission computed tomography (SPECT) and CT.

DETAILED DESCRIPTION

The present invention provides a method for simultaneous CT scanning and PET scanning with compensation for patient respiratory motion, such that registration between CT images and PET images is corrected for artifacts caused by such respiratory motion.

Figure 1:
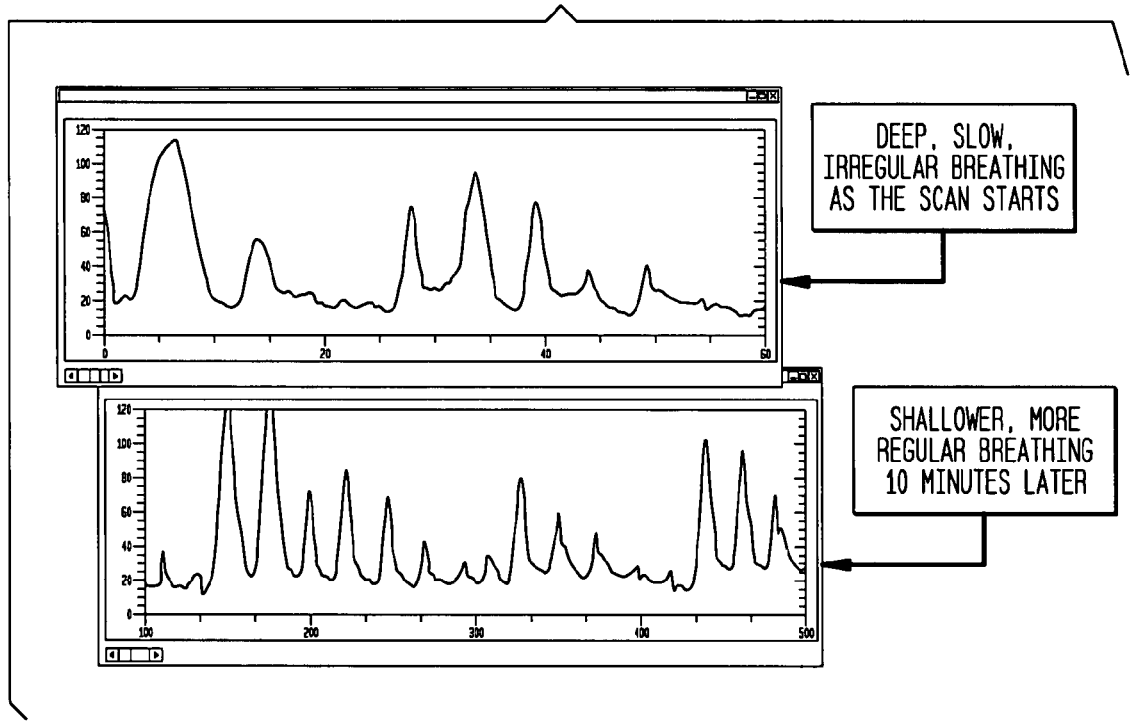
FIG. 1 shows strain gauge signal traces of a patient's respiration over a period of time corresponding to an image scanning procedure.
Figure 2:
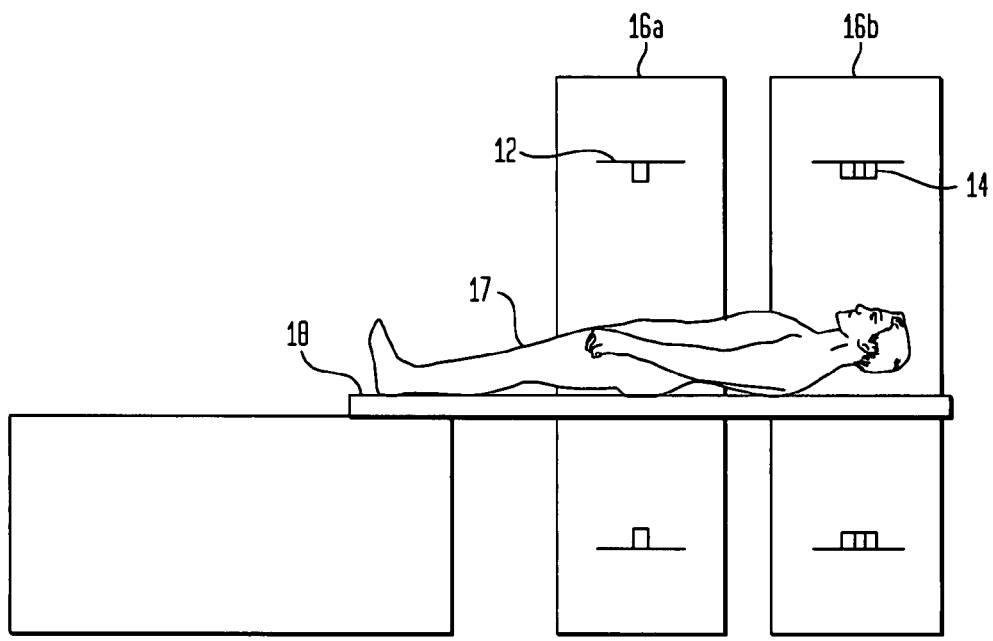
FIG. 2 shows an imaging device for simultaneously performing CT and PET scanning, which can be used in accordance with the present invention.

The invention can be carried using a CT scanner and a PET scanner that can acquire image data in list mode. FIG. 2 shows one example of a combination PET/CT apparatus that may be used with the present invention. The apparatus includes a CT scanner 12 provided in a gantry 16a and a PET scanner 14 provided in a gantry 16b. A patient 17 lies on a movable patient bed 18, that is movable between the gantries. Alternately, the CT scanner and PET scanner may be combined together in a single gantry.

The CT scanner 12 can be operated both normally and with triggering, and also can be configured to acquire a topogram. As per standard PET/CT imaging protocols, after the patient has received an appropriate dose of radiopharmaceutical (e.g., FDG), the patient is positioned on the patient bed 18, and an initial topogram is acquired. The topogram is used subsequently to define the examination range for the PET/CT image acquisition.

A processor (not shown) also is provided to receive the signals from the strain gauge and to insert the strain measurement signals into the PET data stream. The processor includes software that converts strain gauge signals in a particular phase of respiration, either inspiration or expiration, into a gating signal for the CT scanner.

In accordance with one embodiment of the invention, after the acquisition of a topogram by the CT scanner, the operator reviews the topogram to determine and set the scanning positional limits for the diagnostic CT and PET scans. Next, a first (normal) CT scan is acquired, in which the patient follows a breathing pattern (e.g. free breathing) as instructed by the clinician. After the completion of the first CT scan, a PET scan is performed, with a strain gauge attached to the patient providing strain level signals, and with PET data acquired in list mode. The strain level signals are correlated with the PET list mode data.

Figure 3:
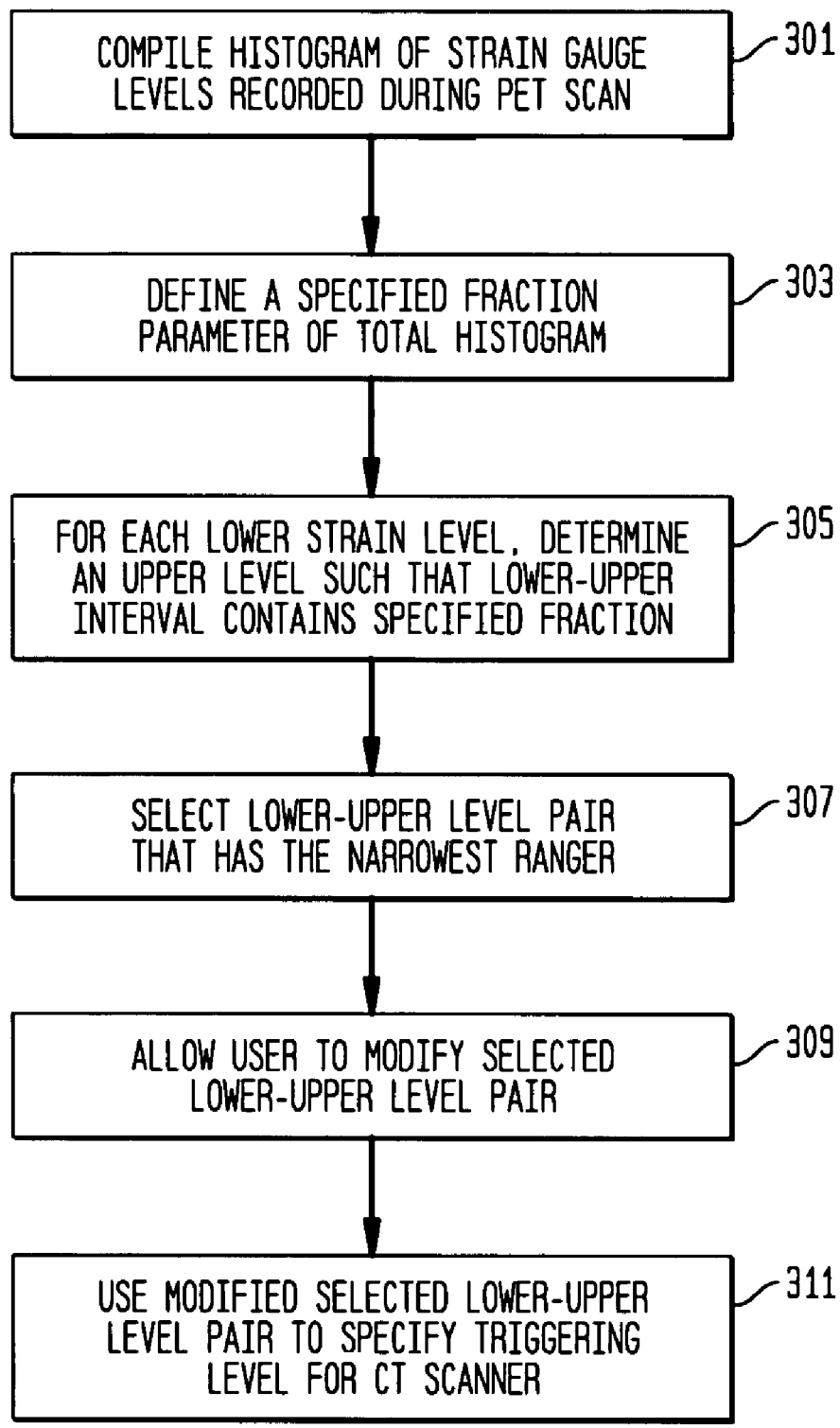
FIG. 3 is a flow diagram of a process for determining an upper and lower strain level pair to be used for developing a CT scan trigger signal in accordance with one embodiment of the invention.
Figure 4:
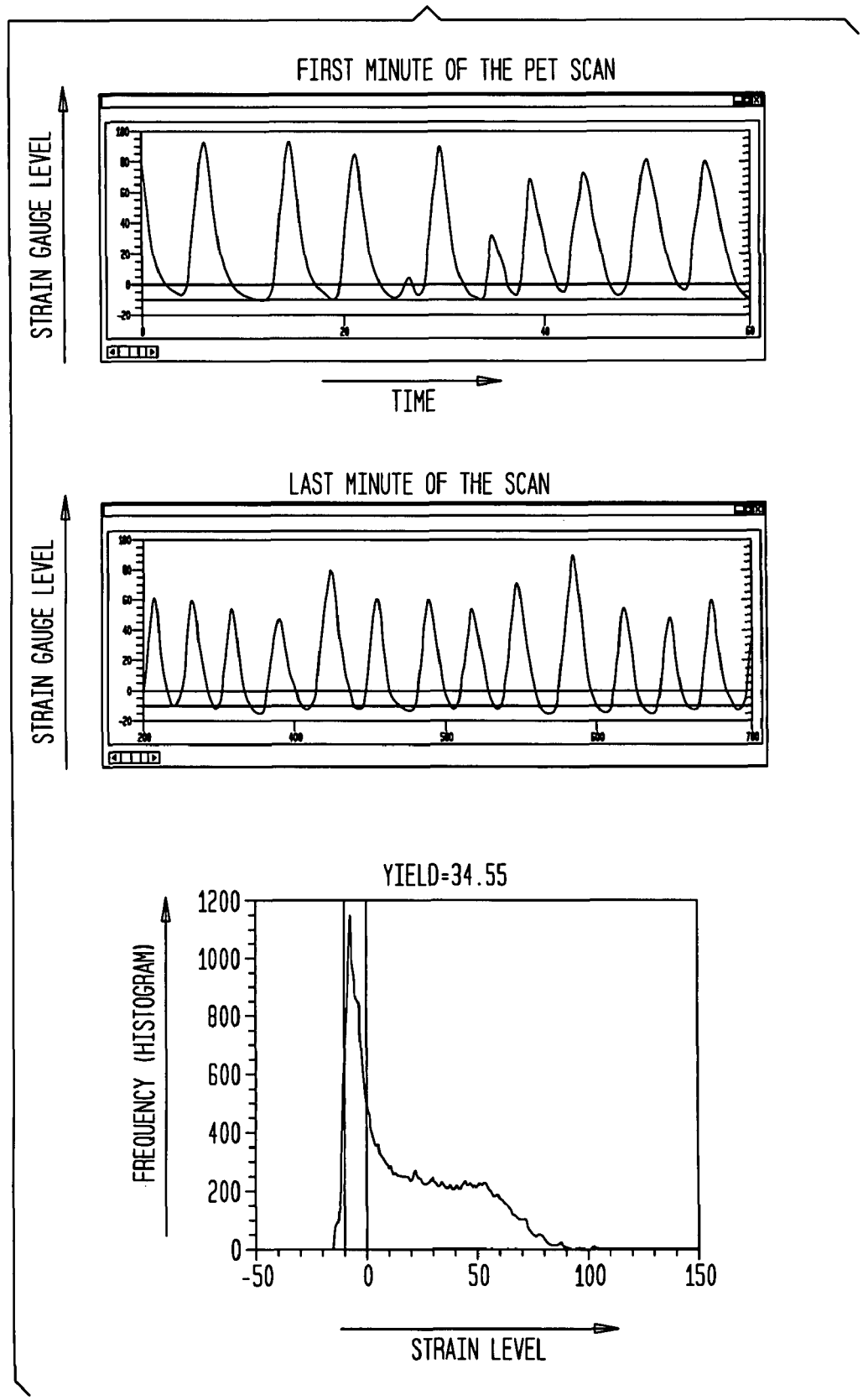
FIG. 4 shows a strain gauge signal level histogram constructed in accordance with the process of FIG. 3.

After the PET list mode data and strain level measurement data are acquired, the procedure advances to a computational process as shown in FIG. 3. In step 301, a histogram of all strain gauge level signals is compiled, as shown in FIG. 4. At step 303, a specified fraction parameter is defined, which is some major fraction of the entire histogram. Next, at step 305 each lower strain level (i.e., strain levels attained at the end of an expiration phase) is considered, and an upper strain level is determined such that the interval defined by the lower and upper levels contains the predefined fraction of the entire histogram. This process is repeated for all lower strain levels.

At step 307, the lower and upper level pair is selected that has the narrowest range of level values, i.e., the lower-upper level combination that minimizes the difference between the two levels. This process leads to an automatic recommendation of a strain levels pair that encompasses a high fraction of the total PET acquisition time, while at the same time corresponding to a relatively small amount of chest excursion. This is illustrated in the PET scan respiration traces shown in FIG. 4.

At step 309, the operator is allowed to modify the recommended strain levels pair, by adjusting if desired either the lower level, upper level, both lower and upper level, or no level adjustment. The final strain levels pair is then outputted at step 311 to be used in developing a trigger signal for a gated CT scan. The operator also is able to specify the scan limits of the patient's anatomy to be scanned by the gated CT scan procedure, by referring to either the topogram or the first CT scan image. Preferably, the triggering level is chosen to provide CT images in the middle of the chest excursion range, in the interval from lower to upper level. With this information, a second, respiratory signal-triggered CT scan is performed.

As a result of the protocols of the invention, two CT series result: a normal CT series that would be used for PET/CT in the absence of respiration information; and a triggered CT series, which represents one phase of patient respiration. Also, two PET series are obtained: a normal PET series based on non-gated PET scan and the non-gated CT scan, which has the best statistics but is affected by motion blur in regions of large respiratory motion; and a motion-frozen PET series based on the lower-to-upper strain excursion interval. This series has attenuation correction based on the gated CT scan and thus has less optimal statistics, but has greatly reduced motion blur and is quantitatively relevant.

It will be clear to one skilled in the art that the above embodiment may be altered in many ways without departing from the scope of the invention. Accordingly, the scope of the invention should be determined by the following claims and their legal equivalents.

For example, as an alternative to the above-described protocol, a gated CT scan could be performed prior to the list mode PET scan. However, in the usual configuration of gated CT this would greatly increase the radiation dose to the patient over a non-gated CT study, would take more time, and could only be performed over a limited anatomical range because of X-ray tube overheating concerns. Further, this imaging technique can be relied on only if the correct respiration levels to be used as triggers are known. In accordance with the invention, after the PET scan is performed with strain gauge attached, there is sufficient information to gate the CT scanner at correct respiration levels.

Finally, as discussed above, while the invention has been described with reference to PET/CT combined modalities, the same problems arise when other imaging modalities are combined, such as SPECT and CT. The histogramming approach also can be applied to CT followed by radiation therapy.

What is claimed is:

1. A method for providing respiration-gated CT image data of a patient, comprising the steps of:
   performing an emission scan of said patient together with measurement of patient respiration level data;
   determining strain levels from the respiration data level data;
   compiling a histogram of the strain levels;
   selecting a fixed fraction parameter, wherein the fixed fraction parameter comprises a predetermined portion of the histogram;
   selecting a lower strain threshold value from measured lower strain levels;
   selecting upper strain threshold values for each measured lower strain level, wherein an interval defined by the upper strain threshold values and the lower strain threshold value includes the predetermined portion of the histogram;
   automatically selecting a final upper strain threshold value and a final lower strain threshold value pair that has a narrowest interval and encompasses the predetermined portion of the histogram; and
   using said automatically selected final lower and upper strain threshold value pair to develop a trigger signal to gate a CT image scan using a respiration signal from said patient to acquire said gated CT image data.

2. The method of claim 1, wherein said emission scan is a PET scan.

3. The method of claim 2, wherein said PET scan is a list-mode scan.

4. The method of claim 2, wherein said step of selecting automatically selecting the final upper strain threshold value and the final lower strain threshold value pair provides means to acquire the gating signal for a minimum number of respiratory movements during a minimum PET acquisition time.

5. The method of claim 1, wherein said emission scan is a SPECT scan.

6. The method of claim 1, wherein said patient respiration measurement is performed with a strain gauge.

7. The method of claim 1, further comprising registering said gated CT image scan with image data from said PET scan.

8. The method of claim 1, further comprising the step of allowing an operator to modify the automatically selected final lower strain threshold value and final upper strain threshold value to be used in development of said trigger signal.

9. A method for combined computed tomography (CT) imaging and emission imaging comprising the steps of:
performing an emission scan of said patient together with measurement of patient respiration level data;
determining strain levels from the respiration level data;
compiling a histogram of the strain levels;
selecting a fixed fraction parameter, wherein the fixed fraction parameter comprises a predetermined portion of the histogram;
selecting a lower strain threshold value from measured lower strain levels;
selecting upper strain threshold values for each measured lower strain level, wherein an interval defined by the upper strain threshold values and the lower strain threshold value includes the predetermined portion of the histogram;
automatically selecting a final upper strain threshold value and a final lower strain threshold value pair that has a narrowest interval and encompasses the predetermined portion of the histogram; and
using said automatically selected final lower and upper strain threshold value pair to develop a trigger signal to gate a CT image scan using a respiration signal from said patient to acquire said gated CT image data.

10. The method of claim 9, wherein said emission scan is a PET scan.

11. The method of claim 10, further comprising the step of registering PET image data of said PET scan with CT image data of said CT scan.

12. The method of claim 9, wherein said emission scan is a SPECT scan.

13. The method of claim 12, further comprising the step of registering SPECT image data of said SPECT scan with CT image data of said CT scan.

* * * * *